US00PP14339P29

(12) United States Plant Patent
Strope

(10) Patent No.: US PP14,339 P2
(45) Date of Patent: Dec. 2, 2003

(54) ARGYRANTHEMUM PLANT NAMED 'BALARGRITE'

(50) Latin Name: *Argyranthemum frutescens*
Varietal Denomination: Balargrite

(75) Inventor: Kerry M. Strope, Jefferson City, MO (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/329,615

(22) Filed: Dec. 26, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Wood, Phillips, Katz, Clark & Mortimer

(57) ABSTRACT

A new and distinct Argyranthemum plant named 'Balargrite', characterized by its white ray florets and yellow disc florets, medium green leaves and upright growth habit.

2 Drawing Sheets

Latin name of the genus and species of plant claimed: *Argyranthemum frutescens.*
Variety denomination: 'Balargrite'.

BACKGROUND OF THE INVENTION

The present invention comprises a new and distinct Argyranthemum plant, botanically known as *Argyranthemum frutescens,* and hereinafter referred to by the cultivar name 'Balargrite'.

The new cultivar is the result of a planned breeding program with the objective being the development of Argyranthemum plants that are freely branching, freely flowering and have a compact, upright growth habit.

The new cultivar is the result of open pollination, with the female parent being the commercially available variety 'Sugar Baby' (U.S. Plant Pat. No. 10,298), characterized by white ray florets and yellow disc florets. The new cultivar was discovered by the inventor during February 2000, in a controlled environment at Arroyo Grande, Calif.

Asexual reproduction of the new cultivar has been carried out at Arroyo Grande, Calif. and West Chicago, Ill. by terminal tip cuttings and has demonstrated that the characteristics of the new cultivar as herein described are firmly fixed and retained through successive generations of such asexual propagation.

SUMMARY OF THE INVENTION

It was found that the cultivar of the present invention:

(a) exhibits white ray florets and yellow disc florets, (b) forms foliage of a medium green color, and (c) exhibits a compact upright growth habit.

The new cultivar of the present invention can be compared to its female parent, 'Sugar Baby'. In side-by-side comparisons, plants of the new cultivar are more floriferous and have larger flowers with slightly longer and narrower ray florets.

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown for 10 weeks in a greenhouse at West Chicago, Ill.

DETAILED BOTANICAL DESCRIPTION

Figure 1:
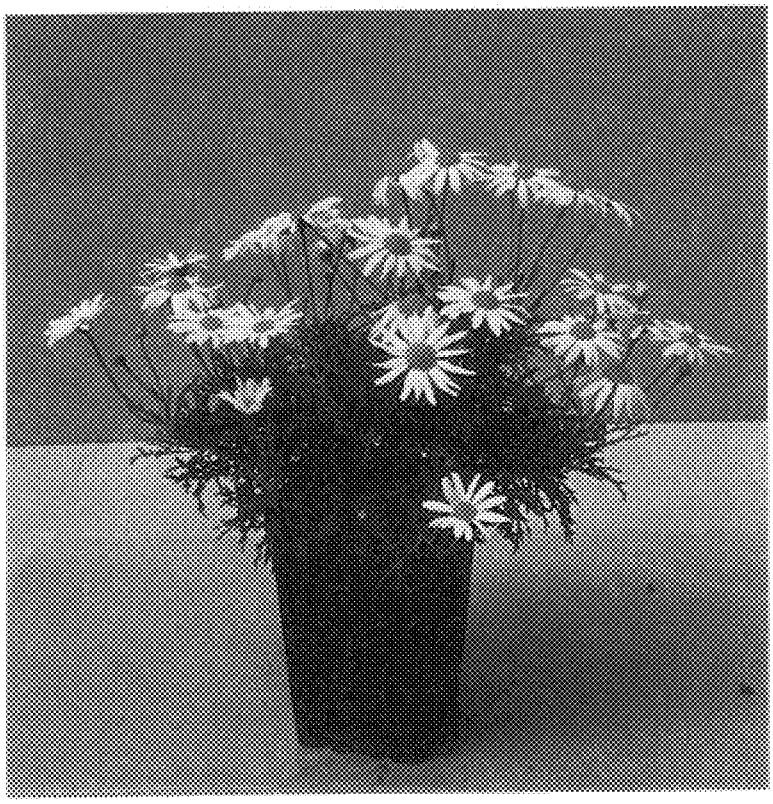
FIG. 1 illustrates the overall growth habit of the new cultivar with one plant per pot.
Figure 2:
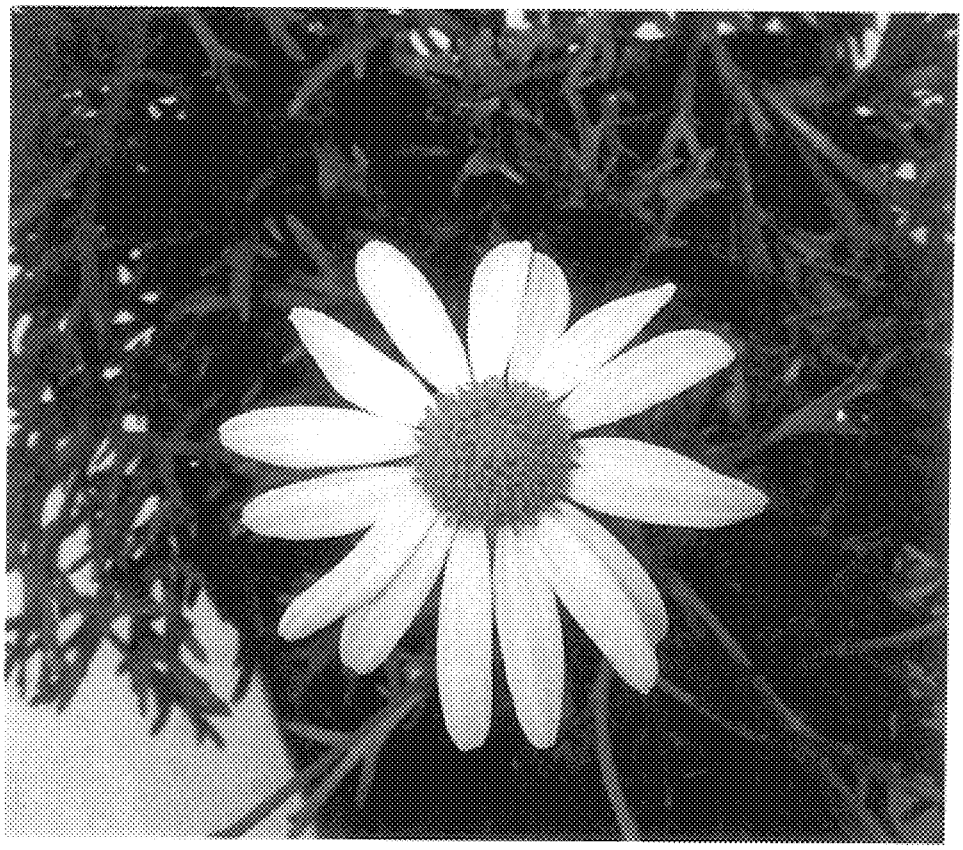
FIG. 2 illustrates a close up of an individual flower of the new cultivar.

The new cultivar has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Apr. 18, 2002. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown utilizing a soilless growth medium and maintaining temperatures of approximately 65° to 78° F. (18° to 25° C.) during the day and approximately 50° to 60° F. (10° to 115° C.) during the night and light levels of 6,000 to 9,000 footcandles. Plants used for the following descriptions and measurements were grown in 10 cm pots for 10 weeks from rooted cuttings.

Classification:
*Botanical.*—*Argyranthemum frutescens* cultivar 'Balargrite'.
Parentage:
*Female parent.*—Commercially available cultivar 'Sugar Baby' (U.S. Plant Pat. No. 10,298).
Propagation:
*Type cutting.*—Terminal tip.

*Time to initiate roots.*—Approximately 7 to 10 days.

*Time to develop roots.*—Approximately 14 to 21 days.

*Root description.*—Fibrous, branching.

Plant description:

*Crop time.*—Approximately 8 weeks in a 10 cm pot.

*Habit of growth.*—Compact. Freely branching. One or two pinches improves branching.

*Form.*—Upright mounded.

*Plant height.*—A mature plant, 10 weeks after the planting of a rooted cutting, commonly measures approximately 18.7 cm in height.

*Plant diameter.*—Approximately 31.6 cm in diameter.

*Branch.*—Number: An average of 8.4 per plant. Length: Approximately 7.2 cm. Diameter: Approximately 4 mm. Texture: Glabrous. Color: 143B. Internode length at middle of branch: Approximately 9 mm.

*Foliage.*—Leaves are non-fragrant, single, alternate and at an acute angle to the stem. Shape: Pinnatified. Margin: Entire. Apex: Acute. Base: Attenuate, clasping. Upper and lower surfaces are glabrous. Leaf length: Approximately 5.4 cm. Leaf width: Approximately 3.5 cm. Color: Upper surface of mature foliage is 137A, lower surface of mature foliage is 137C. Venation of both upper and lower surfaces is closest to 144B.

Flowering description:

*Flowering habit.*—Freely flowering.

*Natural flowering season.*—Year round in greenhouse environment and spring through autumn in outdoor garden.

*Inflorescence type.*—Single composite. Persistent.

*Inflorescence description.*—Shape: Round. Diameter: Approximately 4.2 cm. Depth: Approximately 1 cm. Florets are arranged acropetally on a capitulum. Aspect: Facing upward or outward. Fragrance: None. Number per plant: Approximately 33.4. Lastingness: Approximately 20 days.

*Ray florets.*—Number: Approximately 21. Aspect: Pointing slightly downward. Texture: Smooth. Arrangement: Imbricate. Shape: Elliptic. Length: Approximately 1.6 cm. Width: Approximately 5 mm. Margin: Entire. Tip: Emarginate. Base: Fused to form tube. Color of upper surface of mature ray floret is 155D. Color of lower surface of mature ray floret is 155D. Fused base is 150A.

*Disc.*—Diameter: Approximately 1.2 cm. Depth: Approximately 6 mm. Number of disc florets: Approximately 144.

*Disc floret.*—Shape: Tubular with five lobes. Margin: Entire. Texture: Glabrous. Length: Approximately 6 mm. Width: Approximately 2 mm.

*Phyllaries.*—Approximately 17, imbricate, arranged in 3 rows. Length: Approximately 6 mm. Width: Approximately 3 mm. Shape: Lanceolate. Color of upper surface: 144A. Color of lower surface: 143B.

*Peduncle.*—Strong, erect and glabrous. Length: Approximately 7 cm. Diameter: Approximately 1 mm. Color: 144A.

*Bud.*—Flat, round, approximately 5 mm in diameter and 6 mm in depth. Color: 165B.

*Reproductive organs.*—Androecium: Present on disc florets only. Stamens. 4. Anthers are 1 mm in length. Pollen amount: Moderate. Pollen color: 17B. Gynoecium: Present on ray and disc florets. One pistil per floret. Pistil length: 2 mm. Stigma shape: 2 parted. Stigma length: Less than 1 mm. Stigma color: 12A. Style length: Less than 1 mm. Style color: 1C. Ovary diameter: 1 mm. Ovary color: N144C.

Seed production: Seed production has not been observed.

Disease resistance: Resistance to pathogens has not been observed.

Hardiness zone: 'Balargrite' is hardy in zones nine (9) and above.

I claim:

1. A new and distinct Argyranthemum plant named 'Balargrite' substantially as herein shown and described, which:

(a) exhibits white ray florets and yellow disc florets, (b) forms foliage of a medium green color, and (c) exhibits an upright growth habit.

* * * * *